United States Patent
Thuilliez et al.

(10) Patent No.: US 8,071,700 B2
(45) Date of Patent: Dec. 6, 2011

(54) BOROHYDRIDE METALLOCENE COMPLEX OF A LANTHANIDE, CATALYTIC SYSTEM INCLUDING SAID COMPLEX, POLYMERIZATION METHOD USING SAME AND ETHYLENE/BUTADIENE COPOLYMER OBTAINED USING SAID METHOD

(75) Inventors: Julien Thuilliez, Clermont-Ferrand (FR); Christophe Boisson, Tramoyes (FR); Roger Spitz, Lyons (FR)

(73) Assignees: Michelin Recherche et Technique S.A, Granges-Paccot (CH); Total Petrochemicals France, Puteaux (FR); Centre National de la Recherche Scientifique, Paris (FR); Ecole Superieure de Chimie-Physique-Electronique de Lyon (CPE), Villeurbanne (FR)

( * ) Notice: Subject to any disclaimer, the term of this patent is extended or adjusted under 35 U.S.C. 154(b) by 213 days.

(21) Appl. No.: 12/084,809

(22) PCT Filed: Oct. 31, 2006

(86) PCT No.: PCT/EP2006/010452
§ 371 (c)(1),
(2), (4) Date: Feb. 2, 2009

(87) PCT Pub. No.: WO2007/054223
PCT Pub. Date: May 18, 2007

(65) Prior Publication Data
US 2009/0182104 A1 Jul. 16, 2009

(30) Foreign Application Priority Data
Nov. 9, 2005 (FR) ..................... 05 11416

(51) Int. Cl.
C07F 17/00 (2006.01)
C07F 5/00 (2006.01)
C08F 36/00 (2006.01)
C08F 4/52 (2006.01)
B01J 31/22 (2006.01)

(52) U.S. Cl. ........ 526/164; 502/103; 502/152; 526/126; 526/132; 526/134; 526/160; 526/335; 526/348; 526/943; 556/7; 556/8; 556/11; 556/12

(58) Field of Classification Search .............. 556/11, 556/12, 7, 8; 502/103, 152; 526/126, 160, 526/164, 132, 134, 335, 348, 943
See application file for complete search history.

(56) References Cited

U.S. PATENT DOCUMENTS

| | | | |
|---|---|---|---|
| 6,569,799 B1 | 5/2003 | Barbotin et al. | |
| 7,547,654 B2 | 6/2009 | Boisson et al. | |
| 2003/0004287 A1 | 1/2003 | Barbotin et al. | |

FOREIGN PATENT DOCUMENTS

| | | |
|---|---|---|
| EP | 1 092 731 | 4/2001 |
| WO | WO 2004/035639 | 4/2004 |
| WO | WO 2005/028526 | 3/2005 |

OTHER PUBLICATIONS

C. Qian et al., "Synthesis of diphenylmethylene bridged fluorenyl cyclopentadienyl lanthanocene complexes with Cs symmetry and crystal structures of the ate complexes [Li(thf)4 ] [LnCl2{ (C13H8) CPh2 (C5H4)}] and Li(thf)4 [Ln(BH4) 2 { (C13H8) CPh2 (C5H4) }] (Ln = Nd or La)", Journal of Chemical Society, Dalton Transactions, pp. 3283-3287, 1999.

M.F. Llauro et al., "Investigation of ethylene/butadiene copolymers microstructure by 1H and 13C NMR", Macromolecules, ACS, vol. 34, No. 18, pp. 6304-6311, 2001.

Barbier-Baudry et al. "Non-hindered ansasamarocenes, versatile catalysts for diene/olefin/polar monomer copolymerisations. What is really the active species?" Journal of Organometallic Chemistry 647 (2002) 167-179 XP004347237.

M. Visseaux et al. "Synthesis and X-ray structure of a borohydrido metallocene of neodymium and its use as pre-catalyst in Nd/Mg dual-component ethylene and isoprene polymerizations" Journal of Organometallic Chemistry 691 (2006) 86-92 XP002393572.

(Continued)

Primary Examiner — Caixia Lu
(74) Attorney, Agent, or Firm — Cozen O'Connor

(57) ABSTRACT

A borohydride metallocene complex of a lanthanide, its process of preparation, a catalytic system incorporating a borohydride metallocene complex and a process for the copolymerization of olefins employing this catalytic system. Such a complex corresponds to one or other of the following formulae A and B:

A:

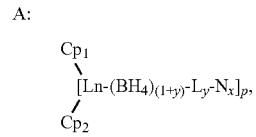

B:

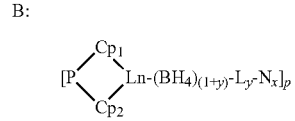

where, in the formula A, two ligands $Cp_1$ and $Cp_2$, each composed of a cyclopentadienyl group, are connected to the lanthanide Ln, such as Nd, and where, in the formula B, a ligand molecule, composed of two cyclopentadienyl groups $Cp_1$ and $Cp_2$ which are connected to one another via a bridge P of formula $MR_1R_2$, where M is an element from group IVa, such as Si, and where $R_1$ and $R_2$, which are identical or different, represent an alkyl group comprising from 1 to 20 carbon atoms, is connected to the lanthanide Ln, where L represents an alkali metal, such as Li, where N represents a molecule of a complexing solvent, such as THF, where x is an integral or non-integral number greater than 0, where p is an integer equal to or greater than 1 and where y is an integer which is equal to or greater than 0.

11 Claims, No Drawings

OTHER PUBLICATIONS

A. V. Khvostov et al. "*ansa*-Ytterbocene(III) chloride and borohydride with a short bridge and bulky substituents: synthesis and crystal structure of [*meso*-$(CH_3)_2Si[3-(CH_3)_3SiC_5H_3]_2$ $Yb(\mu_2-Cl]_2$ and *meso*-$(CH_3)_2Si[3-(CH_3)_3SiC_5H_3]_2$ $Yb[(\mu_2-H)_3BH](THF)$" Journal of Organometallic Chemistry 589 (1990) 222-225 XP002466011.

Qian et al. "The first example of a dinuclear anionic lanthanoidocene complex: $[K(18\text{-crown-}6)\{(C_{13}H_8)CPh_2(C_5H_4)Nd(BH_4)_2\}]_2$ $C_4H_8O_2$" Journal of Organometallic Chemistry 626 (2001) 171-175.

Qian et al. "Synthesis of diphenylmethylene bridged fluorenyl cyclopentadieny lanthanocene complexes with $C_s$ symmetry and crystal structures of the ate complexes $[Li(thf)_4][LnCl_2\{(C_{13}H_8)CPh_2(C_5H_4)\}]$ and $[Li(thf)_4][Ln(BH_4)_2\{(C_{13}H_8)CPh_2(C_5H_4)\}]$ (Ln = Nd or La)" J. Chem. Soc., Dalton Trans., 1999, 3283-3287 XP00239169.

Thomson "C:\EPOPROGS/SEA\.\.. \.. \ epodata\sea\eplogf\internal+.log" printed Aug. 29, 2007 08:21:11 p. 1 XP002447599.

A. V. Khvostov et al. Synthesis and structural study of the ate-complex rac-$(CH_3)_2C(C_5H_3-3-Si(CH_3)_3)_2$ $Yb(\mu_2-Cl)_2$ $Li(Oet_2)_2$ and the polymeric compound $\{rac-(CH_3)_2C(C_5H_3-3-Si(CH_3)_3)_2$ $Yb(\mu_2-H)_2$ $Yb[(\mu_2-H)_2B(\mu_2-H)_2]_2$ $Li(THF)_2\}_\infty$ Journal of Organometallic Chemistry 564 (1998) 5-12 XP 004146039.

BOROHYDRIDE METALLOCENE COMPLEX OF A LANTHANIDE, CATALYTIC SYSTEM INCLUDING SAID COMPLEX, POLYMERIZATION METHOD USING SAME AND ETHYLENE/BUTADIENE COPOLYMER OBTAINED USING SAID METHOD

RELATED APPLICATIONS

This is a U.S. National Phase Application under 35 USC 371 of International Application PCT/EP2006/010452, filed on Oct. 31, 2006.

This application claims the priority of French patent application no. 05/11416 filed Nov. 9, 2005, the subject matter of which is hereby incorporated by reference.

FIELD OF THE INVENTION

The present invention relates to a borohydride metallocene complex of a lanthanide, to its process of preparation, to a catalytic system incorporating a borohydride metallocene complex of a lanthanide and to a process for the polymerization of at least one olefin using such a catalytic system.

BACKGROUND OF THE INVENTION

It is known to use catalytic systems based on halogenated metallocene complexes of lanthanides for copolymerizing ethylene and a conjugated diene.

The document EP-A-1 092 731 teaches the use, in producing copolymers of ethylene and a conjugated diene, of a catalytic system comprising:

on the one hand, an organometallic complex represented by one of the following generic formulae A or B:

A:

B:

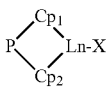

where Ln represents a lanthanide metal having an atomic number which can range from 57 to 71, where X represents a halogen which can be chlorine, fluorine, bromine or iodine, where $Cp_1$ and $Cp_2$ each comprise a cyclopentadienyl or fluorenyl group which is substituted or unsubstituted and where P is a bridge corresponding to the formula $MR_1R_2$, where M is an element from Group IVa of the Periodic Table of the Elements and where $R_1$ and $R_2$ represent an alkyl group comprising from 1 to 20 carbon atoms, and on the other hand, a cocatalyst which is chosen from a group consisting of an alkylmagnesium, alkyllithium, alkylaluminium, and a Grignard reagent or which is composed of a mixture of these constituents.

The document Patent WO-A-2004/035639 on behalf of the Applicants teaches the use, in producing copolymers of ethylene and butadiene, of a catalytic system comprising:

(i) a lanthanide metallocene complex represented by one or other of the following formulae:

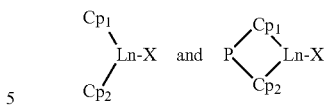

where Ln represents a lanthanide metal having an atomic number which can range from 57 to 71, where X represents a halogen which can be chlorine, fluorine, bromine or iodine, where, in the first formula, two identical or different ligand molecules $Cp_1$ and $Cp_2$, each composed of a fluorenyl group which is substituted or unsubstituted, are connected to the said metal Ln, and where, in the second formula, a ligand molecule composed of two identical or different fluorenyl groups $Cp_1$ and $Cp_2$ which are substituted or unsubstituted and which are connected to one another via a bridge P corresponding to the formula $MR_1R_2$, where M is an element from Group IVa of the Periodic Table of the Elements and where $R_1$ and $R_2$ represent an alkyl group comprising from 1 to 20 carbon atoms, is connected to the said metal Ln, and (ii) a cocatalyst belonging to the group consisting of an alkylmagnesium, an alkyllithium, an alkylaluminium, and a Grignard reagent or which is composed of a mixture of these constituents.

Other catalytic systems based on monocyclopentadienyl complexes of lanthanide borohydride type are known in particular in the literature for the homopolymerization of diolefins.

Mention may be made, for example, of the paper by D. Barbier-Baudry, O. Blacque, A. Hafid, A. Nyassi, H. Sitzmann and M. Visseaux, *European Journal of Inorganic Chemistry* 2000, 2333-2336, which mentions a complex of formula $(C_5H(iPr)_4)Ln(BH_4)_2(THF)$ including a monocyclopentadienyl ligand substituted by an isopropyl group (iPr), where THF is tetrahydrofuran, for the homopolymerization of isoprene or styrene after alkylation by a cocatalyst of organolithium type.

More recently, the paper by F. Bonnet, M. Visseaux, A. Pereira and D. Barbier-Baudry, *Macromolecules*, 2005, 38, 3162-3169, disclosed the use of a similar complex of formula $(C_5Me_4(nPr))Nd(BH_4)_2(THF)_2$ including a pentasubstituted monocyclopentadienyl ligand, where nPr is an n-propyl group, in the stereospecific 1,4-trans polymerization of isoprene after alkylation by a cocatalyst of dialkylmagnesium type.

Mention may also be made of the studies by M. Visseaux et al., Journal of Organometallic Chemistry, 691 (2006), pages 86-92, which have disclosed that the metallocene $CP*_2Nd(BH_4)(THF)$, when it is used in combination with butylethylmagnesium, even in the presence of a large excess of THF, constitutes a very active catalyst for ethylene and, in the presence of a stoichiometric amount of butylethylmagnesium, makes possible the stereospecific 1,4-trans polymerization of isoprene.

The Chinese patent document 1 286 256 discloses, as polymerization catalysts for the synthesis of polymethacrylates, a borohydride metallocene complex of a lanthanide comprising a ligand molecule composed of a fluorenyl group corresponding to the following formula:

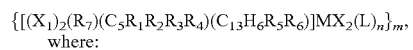

where:

$X_1$ represents an alkyl group having from 1 to 4 carbon atoms or a phenyl group, $X_2$ represents $C_1$, $BH_4$, H, an alkyl group having from 1 to 4 carbon atoms, $N[Si(CH_3)_3]_2$, $CH_2[Si(CH_3)_3]$ or tetrahydrofuran, $R_1$, $R_3$ and $R_4$ represent H or the $CH_3$ radical, $R_2$ represents H, $R_5$ and $R_6$ represent H, an alkyl group having from 1 to 4 carbon atoms or $Si(CH_3)_3$, $R_7$ represents Si, C, Ge or Sn, M represents a lanthanide, yttrium or scandium, L represents $Si(CH_3)_3$, $Li(THF)_4$, [crown ether Y] or [crown ether Y]-2,4-epoxyhexacycle, n represents 0 or 1 and m=1 or 2 (if m=2, n=0), Y is a monovalent metal.

Another recent research route has concerned borohydride metallocene complexes of lanthanides including a ligand based on two cyclopentadienyl groups. Mention may be made, for example, of the studies by S. M. Cendrowski-Guillaume et al., Organometallics, 2000, 19, 5654-5660, and Macromolecules, 2003, 36, 54-60, which have disclosed the use of such a metallocene complex, of formula $(C_5Me_5)_2Sm(BH_4)(THF)$, where Me is a methyl group and where Sm is samarium, for specifically catalysing the polymerization of ε-caprolactone by ring opening.

SUMMARY OF THE INVENTION

One object of the present invention is to achieve the copolymerization of olefins and conjugated dienes using borohydrate metallocene complexes of lanthanides.

This and other objects are attained in accordance with one aspect of the present invention directed to a borohydride metallocene complex of a lanthanide corresponding to one or other of the following two formulae A and B:

A:

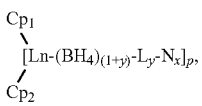

B:

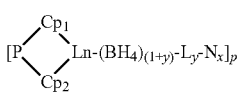

where Ln is a lanthanide having an atomic number of between 57 and 71 inclusive, where, in the formula A, two ligands $Cp_1$ and $Cp_2$, each chosen from identical or different and substituted or unsubstituted cyclopentadienyl or fluorenyl groups, it not being possible, however, for $Cp_1$ and $Cp_2$ to represent two fluorenyl groups, are connected to Ln, where, in the formula B, a ligand, composed of two groups $Cp_1$ and $Cp_2$ which are chosen from identical or different and substituted or unsubstituted cyclopentadienyl or fluorenyl groups, it not being possible, however, for $Cp_1$ and $Cp_2$ to represent two fluorenyl groups, and which are connected to one another via a bridge P corresponding to the formula $MR_1R_2$, where M is an element from Group IVa of the Periodic Table of the Elements and where $R_1$ and $R_2$, which are identical or different, represent an alkyl group comprising from 1 to 20 carbon atoms, is connected to Ln, where L represents an alkali metal chosen from the group consisting of lithium, sodium and potassium, where N represents a molecule of a complexing solvent, such as an ether, where x is an integral or non-integral number which is greater than 0, where y is an integer which is equal to or greater than 0 and where p is an integer which is equal to 1 or 2, can be used in combination with an alkylation cocatalyst chosen from the group consisting of an alkylmagnesium, an alkyllithium, a Grignard reagent and a mixture of an alkyllithium and of an alkylaluminium for the copolymerization of olefins and in particular for the copolymerization of monoolefins and conjugated dienes and more specifically still for producing, with a high catalytic activity, copolymers of ethylene and butadiene.

It should be noted that the borohydride metallocene complex of a lanthanide according to the invention corresponding to the formula A in which, when y is equal to or greater than 1, and in which the two ligands $Cp_1$ and $Cp_2$, which are identical or different, are either each composed of a substituted or unsubstituted cyclopentadienyl group or composed of a substituted or unsubstituted cyclopentadienyl or substituted or unsubstituted fluorenyl group or in which, when y is equal to 0, and in which the two ligands $Cp_1$ and $Cp_2$ are respectively composed of a substituted or unsubstituted cyclopentadienyl group and of a substituted or unsubstituted fluorenyl group, and also the metallocene complex corresponding to the formula B in which, when y is equal to 0, and the two ligands $Cp_1$ and $Cp_2$, which are identical or different, each composed of a group chosen from substituted or unsubstituted cyclopentadienyl and substituted or unsubstituted fluorenyl groups, is, to the knowledge of the Applicants, novel and the very first to date which makes it possible to copolymerize several olefins or at least one olefin with at least one conjugated diene, in combination with an alkylation cocatalyst chosen from the group consisting of an alkylmagnesium, an alkyllithium, a Grignard reagent and a mixture of an alkyllithium and of an alkylaluminium.

In the complexes corresponding to the formulae A and B, p is equal to 1 according to a preferred embodiment.

The complex according to an embodiment of the invention is obtained by a preparation process comprising the reaction of a ligand salt of formula $Cp_1Cp_2$-$L_2$ or P-$Cp_1Cp_2$-$L_2$ and of a lanthanide Ln tris(borohydride) dissolved in the complexing solvent and of formula $Ln(BH_4)_3N_3$.

According to one embodiment of the invention, this preparation process comprises running, at ambient temperature, the said ligand salt, dissolved in another solvent, such as diethyl ether, onto the said solution of lanthanide tris(borohydride), in the form dissolved in this other solvent, stirring the solution at ambient temperature, filtering the stirred solution, concentrating the filtrate and/or drying the product, and optionally adding a poor solvent to the concentrate in order to precipitate the product.

The complexes which correspond specifically to the formula B, of type bridged via the bridge of formula $MR_1R_2$ in which the element M is preferably silicon and $R_1$ and $R_2$ are advantageously a methyl group, and more advantageously the complex corresponding to the formula:

B′:

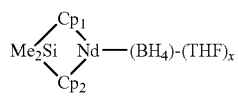

where $Cp_1$ and $Cp_2$ are chosen from identical or different and substituted or unsubstituted cyclopentadienyl groups, it being possible for $Cp_2$ in addition to represent a substituted or unsubstituted fluorenyl group, which are devoid of alkali metal, can advantageously be used, in combination with an alkylation cocatalyst, as catalyst for the polymerization of olefins and in particular for the copolymerization of monoolefins and conjugated dienes and more specifically still for the production, with a good catalytic activity, of copolymers of ethylene and butadiene.

Advantageously, in the said complex, $Cp_1$ represents an unsubstituted cyclopentadienyl group of formula $C_5H_4$ and $Cp_2$ represents a cyclopentadienyl group substituted by a trimethylsilyl group of formula $C_5H_3(Si(CH_3)_3)$.

The complexes which correspond to the formulae A and B are prepared by any process known per se and described in the literature.

Advantageously, the said cocatalyst is butyloctylmagnesium.

The Applicant has discovered that a catalytic system based on a metallocene complex corresponding to the formulae A and B, and preferably B', advantageously makes it possible to copolymerize at least two olefins, such as monoolefins and/or diolefins, which was not known in the prior art with catalytic systems based on a metallocene complex of lanthanide borohydride type.

Another aspect of the invention relates to a process for the copolymerization according to the invention of at least one olefinic monomer, such as a monoolefin, with at least one diolefin which comprises a reaction of the said catalytic system based on a metallocene complex corresponding to the formulae A and B, and preferably B', in the presence of the said monomers and this reaction is preferably carried out in suspension or in solution in a hydrocarbon solvent, such as toluene, and at a temperature of between −20° C. and 120° C.

This reaction can be carried out under a variable pressure, preferably ranging from 1 bar to 50 bar, and, also preferably, at a temperature preferably of between 20° C. and 90° C.

The copolymerization process preferably comprises:

(i) the preliminary preparation of the said catalytic system outside the polymerization medium by reacting the said complex with the said cocatalyst, then (ii) the reaction of the catalytic system obtained in (i) in the presence of the monomers to be copolymerized.

In an alternative form, it should be noted, however, that the catalytic system might be formed in situ in the polymerization medium.

According to a particularly advantageous embodiment of the invention, this process comprises the copolymerization of ethylene and butadiene in order to obtain an ethylene/butadiene copolymer in which:

the molar level of units resulting from butadiene is advantageously greater than 24% and more advantageously still equal to or greater than 45%, and in which the units resulting from butadiene comprise 1,2 (vinyl) links and very predominantly 1,4 links, that is to say equal to or greater than 87%.

According to one characteristic of the invention, use is made of a cocatalyst/complex molar ratio of less than or equal to 10 and advantageously of less than or equal to 5.

Advantageously, the copolymers according to the invention furthermore exhibit a polydispersity index PI which is less than 2.5 and more advantageously still less than or equal to 2.0. Following the example of the molecular weights Mn, the polydispersity indices PI were determined in the present description by steric exclusion chromatography (see the appended Annex 1).

The abovementioned characteristics of the present invention, and others, will be better understood on reading the following description of several exemplary embodiments of the invention.

DETAILED DESCRIPTION OF THE PREFERRED EMBODIMENTS

For all the following examples, the procedure was carried out under argon and the solvents used were dried beforehand by a reaction with sodium, followed by distillation, or else over a 3 Å molecular sieve while flushing with argon.

All the metallocene complexes synthesised below were analysed by $^1H$ NMR in $d_8$-THF at a temperature of 22° C. using a "Bruker DRX 300" spectrometer at a frequency of 300 MHz.

The microstructure of each copolymer obtained in these examples was determined by the $^1H$ NMR and $^{13}C$ NMR techniques described in the appended Annex 2. To this end, use is made of a "Bruker DRX 400" spectrometer at frequencies of 400 MHz for the $^1H$ NMR technique and of 100.6 MHz for the $^{13}C$ NMR technique. The spectra were acquired using a 5 mm "QNP" probe at a temperature of 363 K. A tetrachloroethylene/perdeuterobenzene mixture (ratio by volume 2:1) was used as solvent.

1) Synthesis of a Complex 1 of Lanthanide Borohydride Metallocene Type According to the Invention of Empirical Formula $[Me_2SiCpFluNd(BH_4)_2Li(THF)]$ ($Cp=C_5H_4$; $Flu=C_{13}H_8$)

a) A salt of empirical formula $[Me_2SiCpFlu]Li_2(THF)_2$ (Me, Cp and Flu respectively being a methyl, cyclopentadienyl and fluorenyl group) was synthesized.

To this end, in a first step, a compound of formula $[Me_2Si(C_2H_5)(C_{13}H_8)]$ was synthesized. A solution of $[C_5H_5][Li]$ (0.98 g, 13.6 mmol) in THF (50 ml) was run at ambient temperature onto a solution of $Me_2Si(C_{13}H_9)Cl$ (1.76 g, 6.8 mmol) in THF (50 ml). The solution was stirred for 4 hours and then hydrolysed with a saturated aqueous ammonium chloride solution $(NH_4^+Cl^-)_{sat}$. The organic phase was washed twice with 30 ml of $(NH_4^+Cl^-)_{sat}$ and then dried over magnesium sulphate. The solvent was subsequently evaporated and the orange oil obtained was dried under vacuum for 8 hours. 1.82 g of $[Me_2Si(C_2H_5)C_{13}H_9)]$ were thus prepared (yield=93%).

7.9 ml of a solution of BuLi (1.6M, 12.6 mmol) were run at ambient temperature onto a solution of $[Me_2Si(C_2H_5)(C_{13}H_9)]$ (1.82 g, 6.3 mmol) in THF (100 ml). The mixture was stirred for 4 hours and then the solvent was evaporated under vacuum. The residue obtained was washed three times with 40 ml of heptane at 0° C. and then dried under vacuum. 2.41 g of dilithium salt were thus obtained (yield 86%).

The product was characterized by proton NMR and its empirical formula is $[Me_2SiCpFlu]Li_2(THF)_2$ (MW=444.55 g.mol$^{-1}$). The assignments are:

$^1H$ NMR ($d_5$-pyridine, 22° C.): δ=1.20 ppm (s, 6H, $Si(CH_3)_2$), 1.58 ppm (m, 8H, β-$CH_2$ of the THF), 3.63 ppm (m, 8H, α-$CH_2$ of the THF), 6.65 ppm (s, 2H, $C_5H_4$), 6.95 ppm (s, 2H, $C_5H_4$), 7.07 ppm (t, $J_{H-H}$=8 Hz, 2H, $C_{13}H_8$), 7.31 ppm (t, $J_{H-H}$=8 Hz, 2H, $C_{13}H_8$), 8.60 ppm (d, $J_{H-H}$=8 Hz, 2H, $C_{13}H_8$), 8.70 ppm (d, $J_{H-H}$=8 Hz, 2H, $C_{13}H_8$).

b) Furthermore, the neodymium borohydride of formula $Nd(BH_4)_3(THF)_3$ was synthesised as described in the paper by S. M. Cendrowski-Guillaume, G. Le Gland, M. Nierlich and M. Ephritikhine, *Organometallics*, 2000, 19, 5654-5660.

c) The complex 1 according to the invention was then synthesised in the following way.

A solution of the salt $[Me_2SiCpFlu]Li_2(THF)_2$ (0.500 g, 1.1 mmol) in THF (50 ml) was run at ambient temperature onto a solution of $Nd(BH_4)_3(THF)_3$ (0.456 g, 1.1 mmol) in THF (50 ml). The mixture was stirred for 12 hours and then the solvent was evaporated under vacuum. The residue was taken up in toluene and then the suspension was filtered. The solvent was evaporated from the filtrate and then the solid residue was washed with twice 20 ml of cold pentane. After drying under vacuum, 0.55 g of green compound was thus obtained.

The product was characterized by proton NMR.

The reaction resulted in the neodymium complex 4 according to the invention of empirical formula:

[Me$_2$SiCpFluNd(BH$_4$)$_2$Li(THF)] (MW=539.42 g.mol$^{-1}$).

The signals obtained by proton NMR in d$_8$-THF are:
$^1$H NMR (d$_8$ THF, 22° C.): δ=-5.8 ppm (br, 2H, CH of C$_5$H$_4$ or C$_{13}$H$_8$), -4.1 ppm (br, 2H, CH of C$_5$H$_4$ or C$_{13}$H$_8$), -1.1 ppm (br, 2H, CH of C$_5$H$_4$ or C$_{13}$H$_8$), 0.8 ppm (br, 2H, CH of C$_5$H$_4$ or C$_{13}$H$_8$), 3.2 ppm (br, 2H, CH of C$_5$H$_4$ or C$_{13}$H$_8$), 4.7 ppm (br, 6H, Si(CH$_3$)$_2$), 14 ppm (br, 2H, CH of C$_5$H$_4$ or C$_{13}$H$_8$), 73 ppm (v br, 8H, Nd(BH$_4$)$_2$).

(br means broad signal (peak spread over 1 to 5 ppm) and v br means very broad signal (peak spread over more than 5 ppm)).

2) Synthesis of a Complex 2 of Lanthanide Borohydride Metallocene Type According to the Invention of Empirical Formula [Me$_2$Si(3-TMS-Cp)FluNd(BH$_4$)(THF)] (TMS=Si(CH$_3$)$_3$; Cp=C$_5$H$_3$; Flu=C$_{13}$H$_8$)

a) The neodymium borohydride of formula Nd(BH$_4$)$_3$(THF)$_3$ was synthesized as described in the paper by S. M. Cendrowski-Guillaume, G. le Gland, M. Nierlich and M. Ephritikhine, *Organometallics*, 2000, 19, 5654-5660.

b) The compound 2 according to the invention was subsequently synthesized in the following way:

A solution of [Me$_3$Si—C$_5$H$_4$][Li] (1.47 g, 10 mmol) in THF (20 ml) was run at ambient temperature onto a solution of Me$_2$Si(C$_{13}$H$_9$)Cl (2.64 g, 10 mmol) in THF (50 ml). The mixture was stirred for 4 hours and then the solution was cooled to -20° C. 12.7 ml of a BuLi solution (1.6M, 20 mmol) were then added. The mixture was brought back to ambient temperature and then stirred for 12 hours.

The resulting solution, which comprises the dilithium salt of Me$_2$Si(3-TMS-C$_5$H$_4$)(C$_{13}$H$_9$), was subsequently run at ambient temperature onto a solution of Nd(BH$_4$)$_3$(THF)$_3$ (4.13 g, 10 mmol) in THF (50 ml). The mixture was kept stirred at ambient temperature for 12 hours and then the solvent was evaporated under vacuum. The residue was taken up in toluene (75 ml) and a white salt was removed by filtration. The solvent was subsequently evaporated from the filtrate. The solid was washed three times with toluene at 0° C. (40 ml). After drying under vacuum, 2.60 g of product existing in the form of a green powder were obtained.

Thus, the reaction resulted in the complex 2, which corresponds to the empirical formula:

[Me$_2$Si(3-TMS-Cp)FluNd(BH$_4$)(THF)] (MW=589.75 g.mol$^{-1}$)

3) Synthesis of a Complex 3 of Lanthanide Borohydride Metallocene Type According to the Invention of Formula Me$_2$Si(3-TMS-CP)$_2$Nd(BH$_4$)(THF)$_2$ (TMS=Si(CH$_3$)$_3$; Cp=C$_5$H$_3$)

a) The neodymium borohydride of formula Nd(BH$_4$)$_3$(THF)$_3$ was synthesized as described in the paper by S. M. Cendrowski-Guillaume, G. le Gland, M. Nierlich and M. Ephritikhine, *Organometallics*, 2000, 19, 5654-5660.

b) The compound 3 according to the invention was subsequently synthesized in the following way:

12.4 ml of a BuLi solution (1.6M, 19.8 mmol) were run onto a solution, cooled to 0° C., of Me$_2$Si(3-TMS-Cp)$_2$ (3.29 g, 9.9 mmol) in THF (100 ml). The mixture was stirred at 5° C. for 30 minutes and then at ambient temperature for 6 hours. This solution was subsequently run onto a solution of Nd(BH$_4$)$_3$(THF)$_3$ (4.00 g, 9.9 mmol) in THF (100 ml). The mixture was stirred at ambient temperature for 12 hours and then the THF was evaporated under vacuum. The residue was taken up in toluene (75 ml) and the resulting suspension was filtered. The filtrate was concentrated and then slowly cooled to a temperature of -20° C. Blue crystals were formed (1.00 g).

The product was analysed by proton NMR. Thus, the reaction resulted in the neodymium complex 3 according to the invention of empirical formula:

[Me$_2$Si(3-TMS-Cp)$_2$Nd(BH$_4$)(THF)$_2$] (M=634 g.mol$^{-1}$).

The signals obtained by proton NMR and their assignments are:
$^1$H NMR (d$_5$-pyridine, 22° C.): δ=14.39 ppm (br, C$_5$H$_3$), -12.65 ppm (br, C$_5$H$_3$), -12.31 ppm (br, C$_5$H$_3$), -11.34 ppm (br, C$_5$H$_3$), -2.80 ppm (s, Si(CH$_3$)$_2$, meso form), -1.18 ppm (s, Si(CH$_3$)$_2$, racemic form), 0.02 ppm (s, Si(CH$_3$)$_2$, meso form), 1.59 and 3.63 ppm (s, 2*8H, 2*THF), 2.59 ppm (s, Si(CH$_3$)$_3$, racemic form), 4.00 ppm (s, Si(CH$_3$)$_3$, meso form), 14.14 ppm (br, C$_5$H$_3$), 20.24 ppm (br, C$_5$H$_3$), 49 ppm (v br, 4H, Nd(BH$_4$)).

(br means broad signal (peak spread over 1 to 5 ppm) and v br means very broad signal (peak spread over more than 5 ppm)).

4) Low-Pressure Copolymerization Tests with the Complexes 1 and 2

The complexes 1 and 2 were used in association with butyloctylmagnesium (abbreviated to "BOMAG") as alkylation cocatalyst for the copolymerization of ethylene and butadiene. Each catalytic system 1 or 2 was prepared by carrying out a prior activation of the complex 1 or 2 by the cocatalyst "BOMAG" according to an Mg cocatalyst/Nd complex molar ratio equal to 5, the activation time being 15 min for all the tests 10-1 to 10-8.

The polymerizations took place in a 250 ml glass reactor in 200 ml of toluene at a temperature of 80° C. and a starting pressure of 4 bar. The monomers were introduced into the medium in the form of gas mixtures comprising 20% and 30% of butadiene. Tests where the mixture of monomers comprises 50% and 75% of butadiene were also carried out. In these cases, the feeding with monomers was carried out by dissolving butadiene under cold conditions in the catalytic solution, followed by addition of ethylene in the gaseous form. The medium is subsequently heated at a temperature of 80° C. The amounts of ethylene and butadiene were determined so that the starting pressure at 80° C. is approximately 4 bar.

After a reaction time t (min), the polymerization is halted by cooling and degassing the reactor and then the copolymer is obtained by precipitation from methanol. After drying, a weight w (g) of copolymer is obtained.

TABLE 1

| Polymerization conditions (complexes 1 and 2) | | | | | | |
|---|---|---|---|---|---|---|
| Tests | Complex | Complex in mg | [Nd] in μmol·l$^{-1}$ | [Mg] in μmol·l$^{-1}$ | % Bd feed | Weight of copolymer w in g | Polym. time |
| 4-1 | 1 | 18.4 | 171 | 1010 | 20 | 3.13 | 10 |
| 4-2 | 1 | 18.6 | 172 | 1045 | 30 | 4.00 | 10 |
| 4-3 | 1 | 18.8 | 174 | 1055 | 50 | 3.80 | 20 |
| 4-4 | 1 | 19.6 | 182 | 1110 | 75 | 0.80 | 20 |
| 4-5 | 2 | 20.1 | 170 | 970 | 20 | 5.40 | 12 |
| 4-6 | 2 | 20.0 | 170 | 965 | 30 | 4.10 | 10 |

TABLE 1-continued

Polymerization conditions (complexes 1 and 2)

| Tests | Complex | Complex in mg | [Nd] in µmol·l⁻¹ | [Mg] in µmol·l⁻¹ | % Bd feed | Weight of copolymer w in g | Polym. time |
|---|---|---|---|---|---|---|---|
| 4-7 | 2 | 19.9 | 169 | 960 | 50 | 4.40 | 30 |
| 4-8 | 2 | 20.9 | 177 | 995 | 75 | 1.70 | 60 |
| 4-9 | 3 | 13.9 | 145 | 2900 | 5 | 3.3 | 92 |

TABLE 2

Activities of the complexes 1 and 2 and macrostructure of the copolymers

| Tests | Activity in g·mol⁻¹·h⁻¹ | Activity in g·g⁻¹·h⁻¹ | Mn in g·mol⁻¹ | PI |
|---|---|---|---|---|
| 4-1 | 458 800 | 850 | 4450 | 2.01 |
| 4-2 | 696 050 | 1290 | 6920 | 1.74 |
| 4-3 | 327 100 | 606 | 8550 | 1.76 |
| 4-4 | 66 050 | 122 | 2100 | 1.59 |
| 4-5 | 792 200 | 1343 | 7200 | 1.82 |
| 4-6 | 725 400 | 1230 | 6880 | 1.60 |
| 4-7 | 260 800 | 442 | 8020 | 1.75 |
| 4-8 | 48 000 | 81 | 3710 | 1.68 |
| 4-9 | 99 000 | 155 | 5400 | 1.56 |

TABLE 3

$^{13}$C NMR characterization of the microstructure of the copolymers

| Tests | Molar % of Bd units in the feed | Molar % of Bd units in the copolymer | Molar % of 1,4 links (of which trans) | Molar % of 1,2 links |
|---|---|---|---|---|
| 4-1 | 20 | 29.2 | 97.1 (-) | 2.9 |
| 4-2 | 30 | 44.5 | 96.9 (98.8) | 3.1 |
| 4-3 | 50 | 49.1 | 95.8 (98.8) | 4.2 |
| 4-4 | 75 | 49.6 | 87.0 (-) | 13.0 |
| 4-5 | 20 | 24.5 | 97.6 (>99) | 2.4 |
| 4-6 | 30 | 39.0 | 96.9 (>99) | 3.1 |
| 4-7 | 50 | 45.2 | 95.9 (>99) | 4.1 |
| 4-8 | 75 | 47.2 | 89.7 (>99) | 10.3 |
| 4-9 | 5 | 9.4 | 97.1 | 2.9 |

In the light of Table 3, it is apparent that the complexes 1 and 2 according to the invention make it possible to obtain ethylene/butadiene copolymers in which the units resulting from butadiene are present according to a molar level of greater than 15%, indeed even 45%, and always comprise 1,4 links according to a very high molar level which is equal to or greater than 87%.

ANNEX 1

Analysis by Steric Exclusion Chromatography of the Copolymers a) For the copolymers which are soluble at ambient temperature in tetrahydrofuran (THF), the molar masses were determined by steric exclusion chromatography in THF. The samples were injected using a "Waters 717" injector and a "Waters 515 HPLC" pump at a flow rate of 1 ml.min⁻¹ into a series of "Polymer Laboratories" columns.

This series of columns, placed in a chamber thermostatically controlled at 45° C., is composed of:
1 precolumn: PL Gel 5 µm,
2 columns: PL Gel 5 µm Mixed C,
1 column: PL Gel 5 µm 500 Å.

Detection was carried out using a "Waters 410" refractometer.

The molar masses were determined by universal calibration using polystyrene standards certified by "Polymer Laboratories" and double detection with refractometer and coupling to the viscometer.

Without being an absolute method, SEC makes it possible to understand the distribution of the molecular weights of a polymer. Starting from commercial products which are standards, the different number-average molecular weights (Mn) and weight-average molecular weights (Mw) can be determined and the polydispersity index calculated (PI=Mw/Mn).

b) For the copolymers which are insoluble at ambient temperature in tetrahydrofuran, the molar masses were determined in 1,2,4-trichlorobenzene. They were first of all dissolved under hot conditions (4 h 00 at 150° C.) and were then injected at 150° C. with a flow rate of 1 ml.min⁻¹ into a "Waters Alliance GPCV 2000" chromatograph equipped with three "Styragel" columns (2 "HT6E" columns and 1 "HT2" column).

Detection was carried out using a "Waters" refractometer.

The molar masses were determined by relative calibration using polystyrene standards certified by "Polymer Laboratories".

The invention claimed is:

1. A catalytic system for the copolymerization of at least two olefins, comprising a metallocene complex of a lanthanide and a cocatalyst chosen from the group consisting of an alkylmagnesium, an alkyllithium, and a mixture of an alkyllithium and of an alkylaluminium, wherein the complex is a borohydride metallocene complex of a lanthanide corresponding to the following formula B:

B:

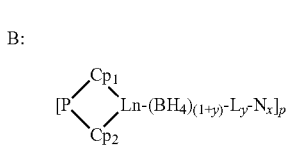

where Ln is a lanthanide having an atomic number of between 57 and 71 inclusive,
where, in the formula B, a ligand composed of two groups $Cp_1$ and $Cp_2$ which are chosen from identical or different and substituted or unsubstituted cyclopentadienyl or fluorenyl groups, with the proviso that $Cp_1$ and $Cp_2$ are not fluorenyl groups at the same time, and which are connected to one another via a bridge P corresponding to the formula $MR_1R_2$, where M is silicon and where $R_1$ and $R_2$, which are identical or different, represent an alkyl group comprising from 1 to 20 carbon atoms, is connected to Ln,
where L represents an alkali metal chosen from the group consisting of lithium, sodium and potassium, where N represents a molecule of a complexing solvent, where x is an integral or non-integral number which is greater than 0, where y is an integer which is equal to or greater than 0 and where p is an integer which is equal to 1 or 2.

2. The catalytic system according to claim 1, wherein the cocatalyst is butyloctylmagnesium.

3. A process for the copolymerization of at least two olefinic monomers, such as a monoolefin and/or a diolefin, by reaction of a catalytic system comprising a metallocene complex of a lanthanide and a cocatalyst chosen from the group consisting of an alkylmagnesium, an alkyllithium, and a mixture of an alkyllithium and of an alkylaluminium, wherein the complex is a borohydride metallocene complex of a lanthanide corresponding to the following formula B:

B:

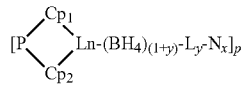

where Ln is a lanthanide having an atomic number of between 57 and 71 inclusive, where, in the formula B, a ligand composed of two groups $Cp_1$ and $Cp_2$ which are chosen from identical or different and substituted or unsubstituted cyclopentadienyl or fluorenyl groups, with the proviso that $Cp_1$ and $Cp_2$ are not fluorenyl groups at the same time, and which are connected to one another via a bridge P corresponding to the formula $MR_1R_2$, where M is silicon and where $R_1$ and $R_2$, which are identical or different, represent an alkyl group comprising from 1 to 20 carbon atoms, is connected to Ln, where L represents an alkali metal chosen from the group consisting of lithium, sodium and potassium, where N represents a molecule of a complexing solvent, where x is an integral or non-integral number which is greater than 0, where y is an integer which is equal to or greater than 0 and where p is an integer which is equal to 1 or 2.

4. The copolymerization process according to claim 3, wherein the lanthanide metallocene complex corresponds to the formula B':

B':

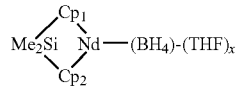

where $Cp_1$ and $Cp_2$ are chosen from identical or different and substituted or unsubstituted cyclopentadienyl groups, it being possible in addition for $Cp_2$ to represent a substituted or unsubstituted fluorenyl group, and x is an integral or non-integral number greater than 0.

5. The copolymerization process according to claim 4, wherein $Cp_1$ and $Cp_2$, each representing a cyclopentadienyl group, are substituted by a trimethylsilyl group.

6. The copolymerization process according to claim 3, further comprising the copolymerization of ethylene and butadiene.

7. The copolymerization process according to claim 3, wherein the molar level of units resulting from butadiene in the copolymer is greater than 24%.

8. The process according to claim 3, wherein the molar level of units resulting from butadiene in the copolymer is equal to or greater than 45%.

9. The copolymerization process according to claim 3, wherein the cocatalyst/complex molar ratio is equal to 10.

10. The copolymerization process according to claim 9, wherein the cocatalyst/complex molar ratio is chosen to be equal to 5.

11. The copolymerization process according to claim 3, comprising:

(i) a preliminary preparation of the catalytic system by reacting the complex with the cocatalyst, then (ii) a reaction in suspension or in solution in a hydrocarbon solvent, and at a temperature of between −20° C. and 120° C. of the catalytic system obtained in (i) in the presence of the monomers to be polymerized.

* * * * *